(12) United States Patent
DiGiacomo

(10) Patent No.: US 10,765,816 B2
(45) Date of Patent: Sep. 8, 2020

(54) SAFETY SYRINGE AND METHODS OF MAKING AND USING SAME

(71) Applicant: Gina DiGiacomo, Kent, CT (US)

(72) Inventor: Gina DiGiacomo, Kent, CT (US)

( * ) Notice: Subject to any disclaimer, the term of this patent is extended or adjusted under 35 U.S.C. 154(b) by 136 days.

(21) Appl. No.: 16/056,925

(22) Filed: Aug. 7, 2018

(65) Prior Publication Data
US 2020/0046911 A1    Feb. 13, 2020

(51) Int. Cl.
*A61M 5/32*    (2006.01)

(52) U.S. Cl.
CPC ........ *A61M 5/3245* (2013.01); *A61M 5/3202* (2013.01); *A61M 5/3257* (2013.01); *A61M 2005/3247* (2013.01)

(58) Field of Classification Search
CPC .... A61M 5/322; A61M 5/3234; A61M 5/326; A61M 5/3243; A61M 5/2033; A61M 5/3271; A61M 5/3257; A61M 5/3213
See application file for complete search history.

(56) References Cited

U.S. PATENT DOCUMENTS

| | | | | |
|---|---|---|---|---|
| 4,573,976 A | * | 3/1986 | Sampson | A61M 5/3269 604/198 |
| 5,026,356 A | * | 6/1991 | Smith | A61M 5/3269 604/192 |
| 5,242,416 A | | 9/1993 | Hutson | |
| 5,360,409 A | * | 11/1994 | Boyd, III | A61M 5/24 604/198 |
| 6,716,199 B2 | * | 4/2004 | DeHarde | A61M 5/3269 604/110 |
| 8,372,044 B2 | * | 2/2013 | Westbye | A61M 5/326 128/919 |
| 8,708,969 B2 | | 4/2014 | Carlyon | |
| 9,789,263 B2 | | 10/2017 | Francavilla | |
| 2005/0101917 A1 | * | 5/2005 | Doyle | A61M 5/326 604/187 |
| 2006/0036217 A1 | * | 2/2006 | Doyle | A61M 5/326 604/198 |
| 2018/0161523 A1 | | 6/2018 | Sanders | |

FOREIGN PATENT DOCUMENTS

WO   WO-2017/046556 A1   8/2016

* cited by examiner

*Primary Examiner* — Manuel A Mendez
(74) *Attorney, Agent, or Firm* — UConn IP Law Clinic; Gabrielle Gelozin Kathryn Ledwith; Daniel Ruskin

(57) ABSTRACT

A syringe safety device is disclosed herein that comprises a shaft configured to support a barrel of a syringe, a guard configured to be disposed inside the shaft before the syringe is used and to extend outwardly from the shaft after the syringe is used, and a lock disposed between the guard and the shaft having a lock head disposed at a first end thereof, the lock head being disposed in a first aperture in the shaft before the syringe is used and in a second aperture in the shaft after the syringe has been used. A method of using the device also is described.

13 Claims, 5 Drawing Sheets

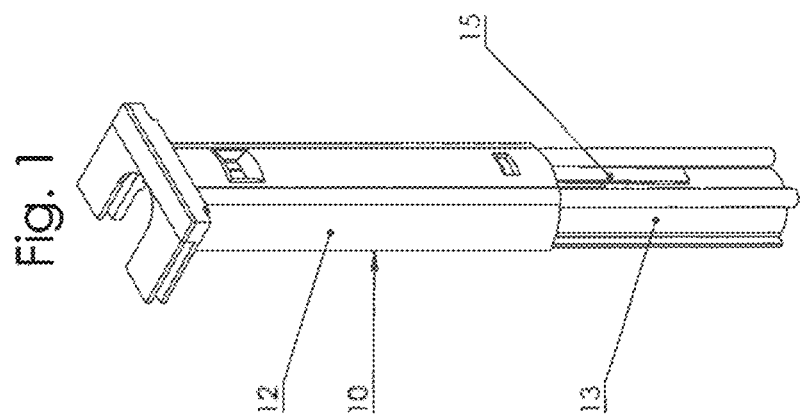
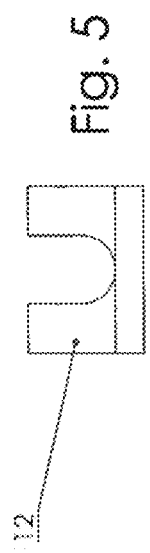
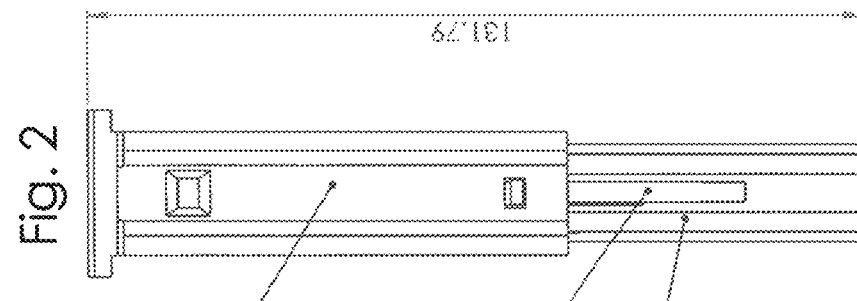
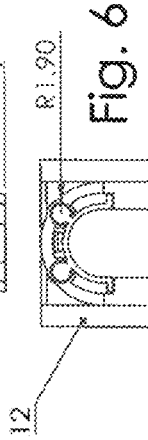
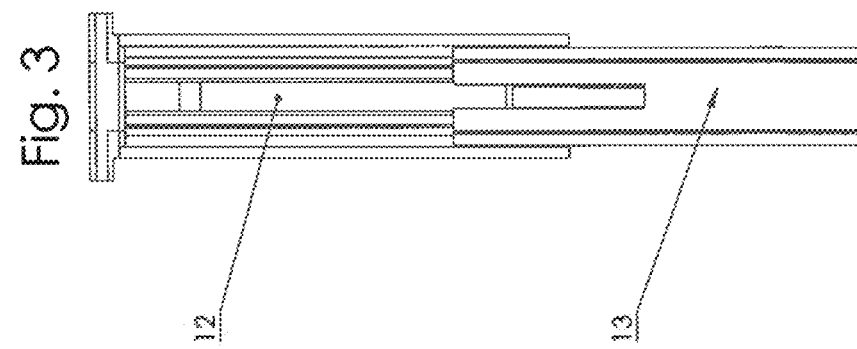

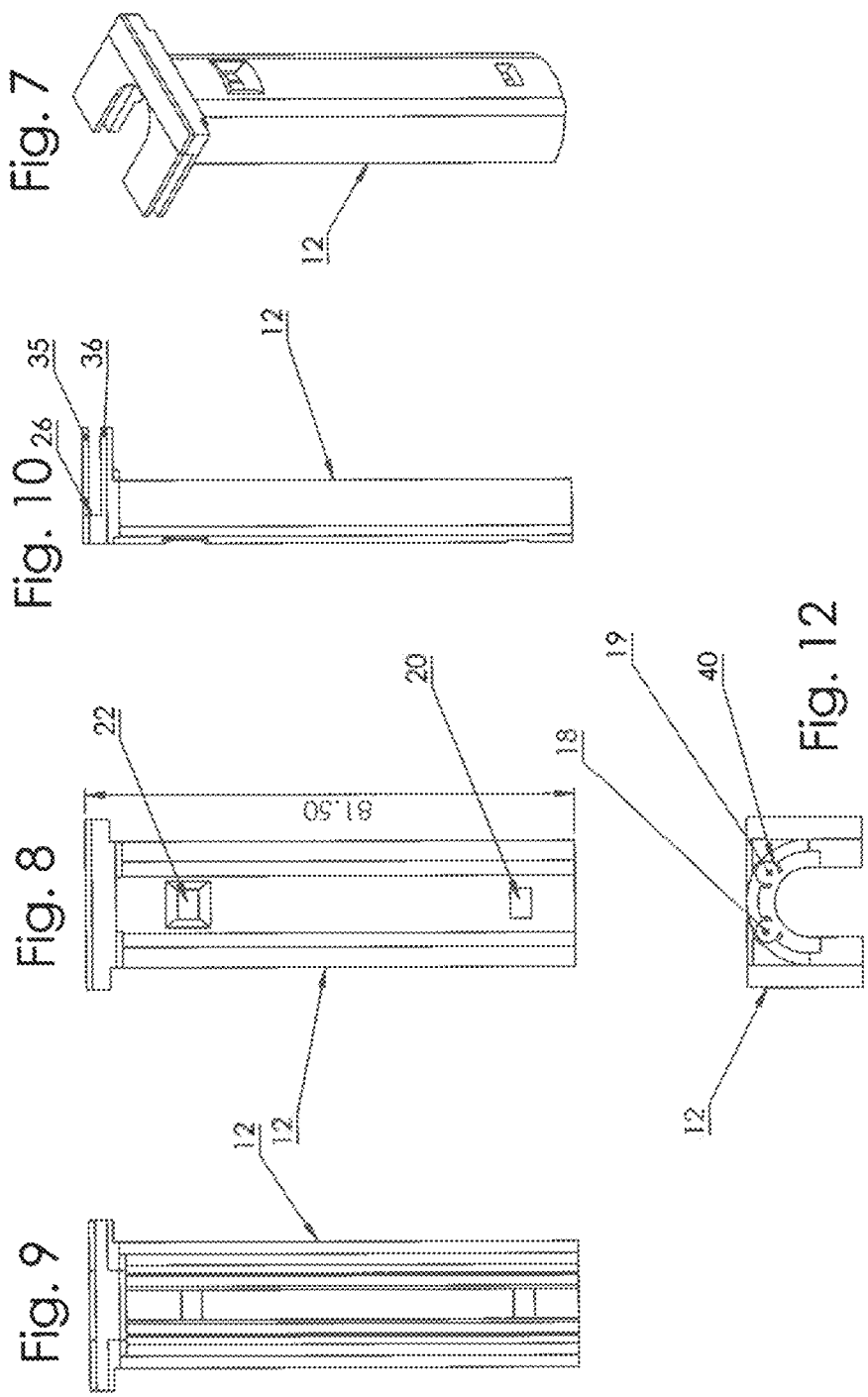

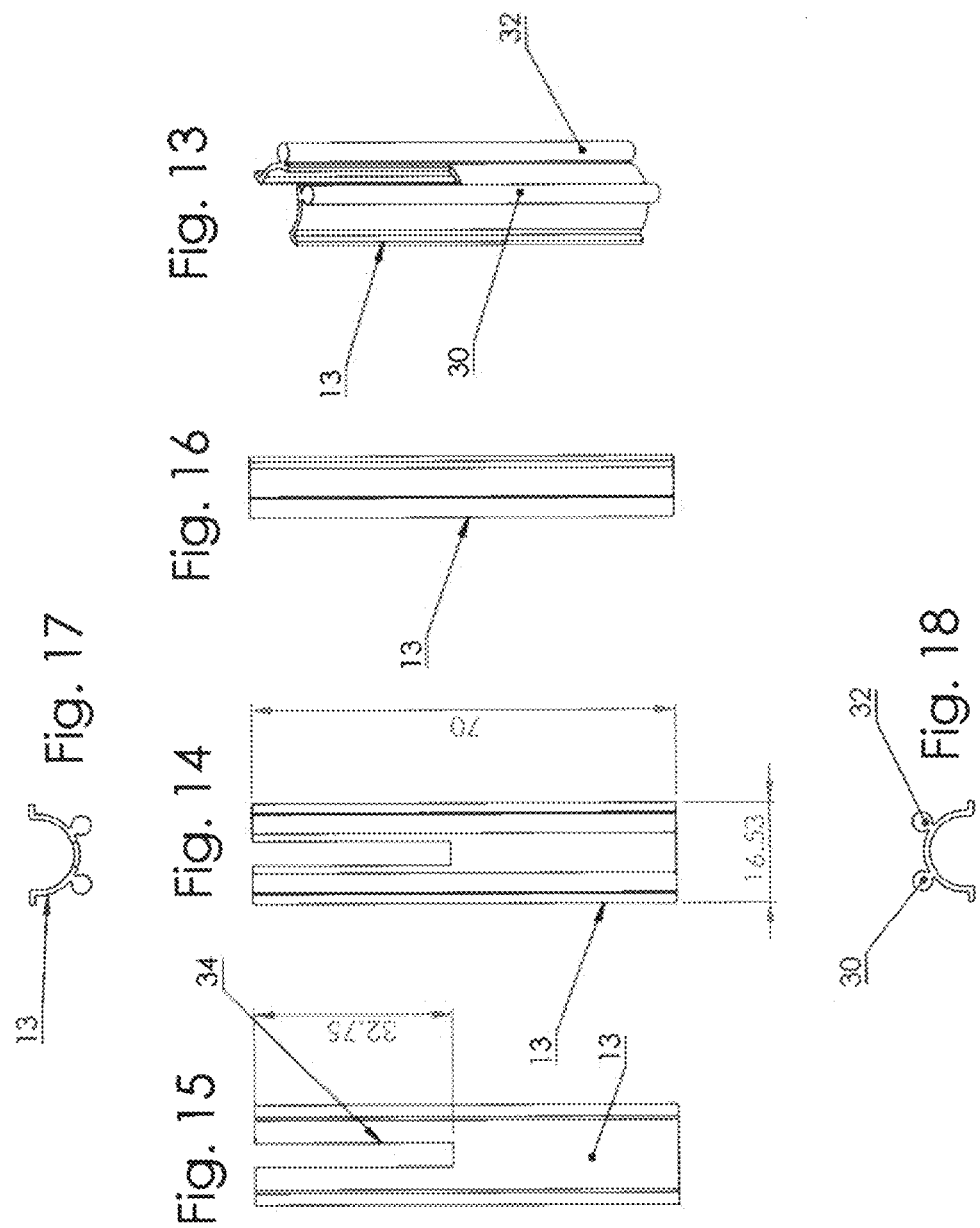

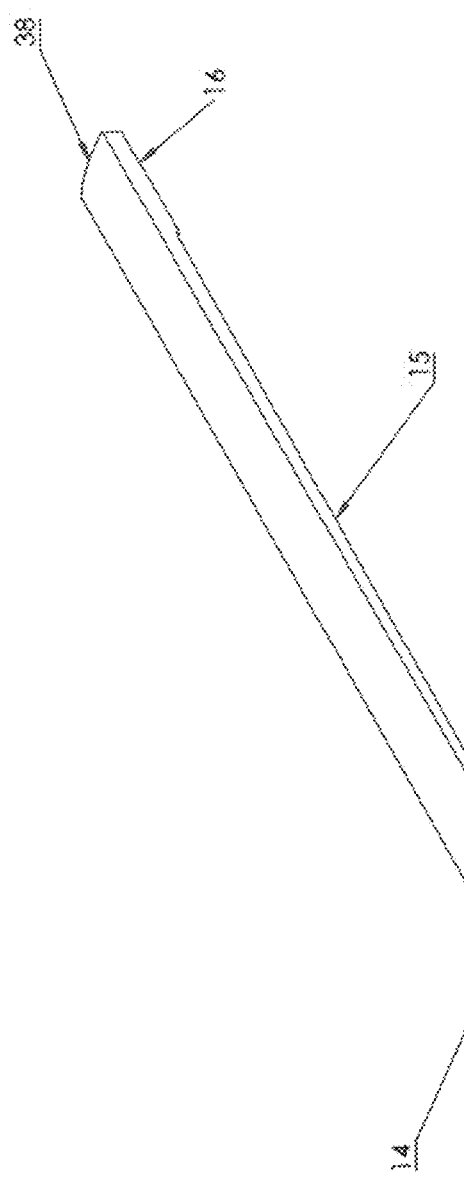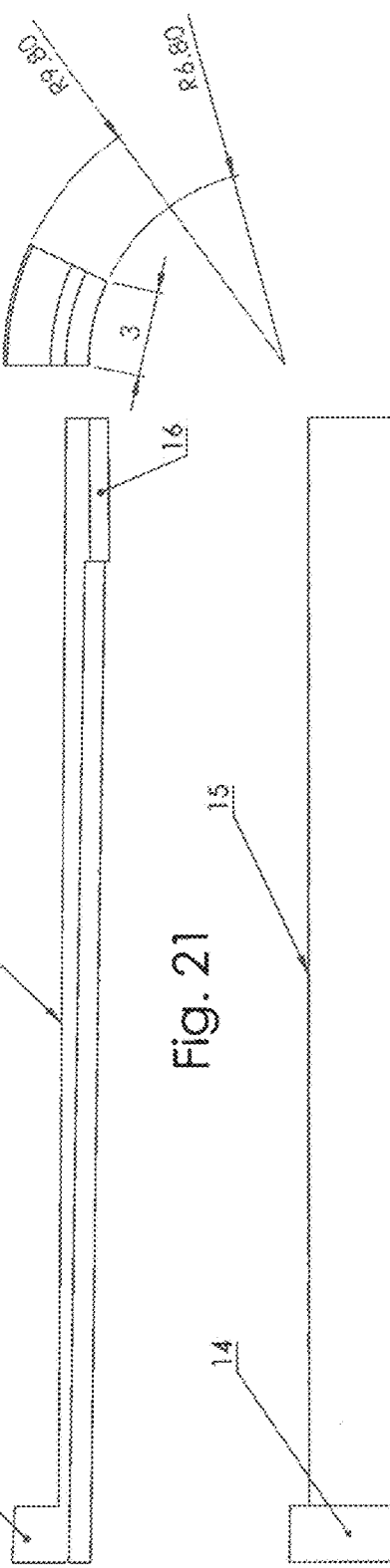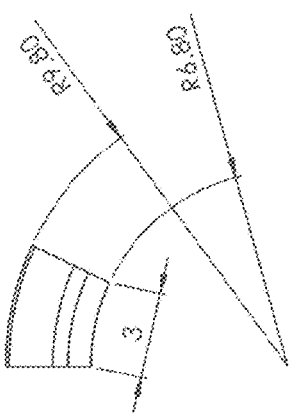

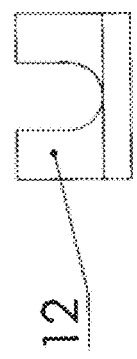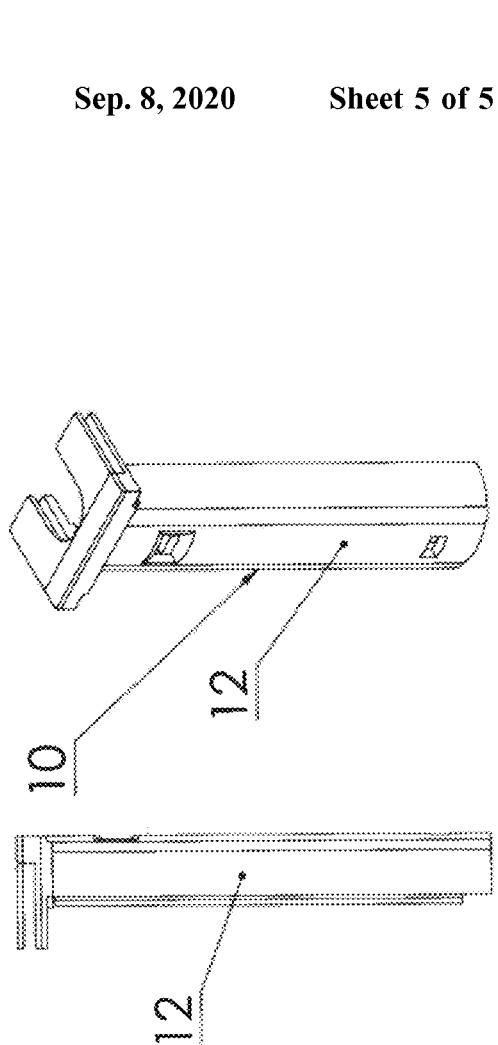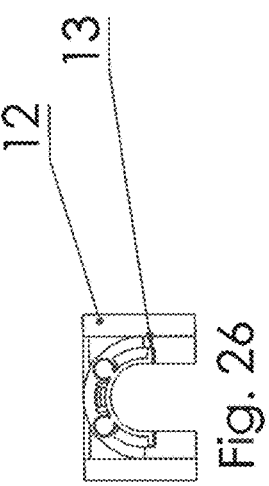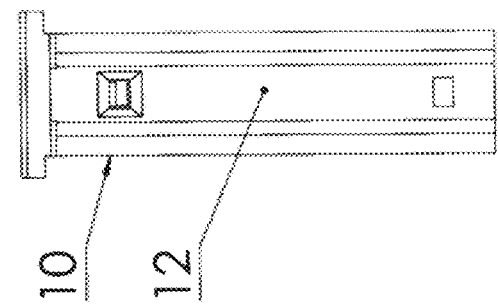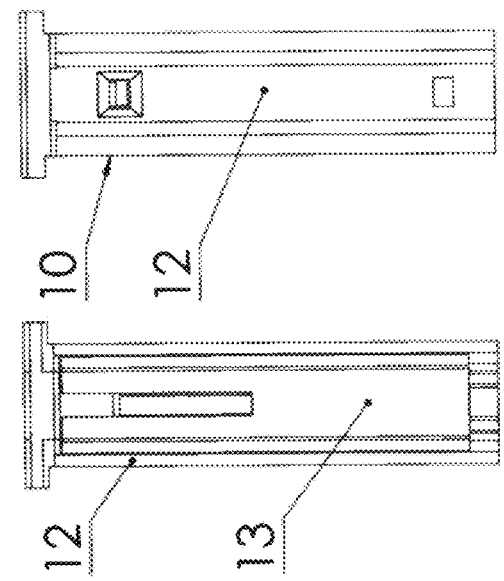

SAFETY SYRINGE AND METHODS OF MAKING AND USING SAME

BACKGROUND

Currently, safety syringes in use by healthcare providers are single use. They provide added protection to users by covering or otherwise making the needle of the syringe inaccessible after it has been used on the patient. This protection is critical in stopping the bloodborne transmission of diseases such as HIV/AIDS, and hepatitis B and C. This however creates a problem where healthcare providers must spend additional funds to create a safer environment for themselves and their patients.

SUMMARY

One embodiment disclosed herein is a syringe safety device, comprising a shaft configured to support a barrel of a syringe, the shaft having an elongated wall with a first aperture, and a second aperture longitudinally spaced from the first aperture, a guard configured to be disposed inside the shaft before the syringe is used and to extend outwardly from the shaft after the syringe is used, and a lock disposed between the guard and the shaft, the lock having a lock head disposed at a first end thereof, the lock head being disposed in the first aperture before the syringe is used and in the second aperture after the syringe is used. In embodiments, the guard is configured to surround a needle after the syringe is used.

In some cases, the guard has an elongated slot providing a clearance space for the lock. In embodiments, the lock includes a guard mount disposed at a second end thereof, the guard mount being configured to keep the guard from leaving the shaft after use. In embodiments, the shaft includes a flange holder configured to support a flange of a syringe during use of the device.

BRIEF DESCRIPTION OF THE DRAWINGS

FIG. 1 is a perspective view of a first embodiment of a syringe safety device.
FIG. 2 is a top view of the device of FIG. 1.
FIG. 3 is a bottom view of the device of FIG. 1.
FIG. 4 is a side view of the device of FIG. 1.
FIG. 5 is a first end view of the device shown in FIG. 1.
FIG. 6 is a second end view of the device shown in FIG. 1.
FIG. 7 is a perspective view of the shaft included in the first embodiment of the syringe safety device.
FIG. 8 is a top view of the shaft of FIG. 7.
FIG. 9 is a bottom view of the shaft of FIG. 7.
FIG. 10 is a side view of the shaft of FIG. 7.
FIG. 11 is a first end view of the shaft shown in FIG. 7.
FIG. 12 is a second end view of the shaft shown in FIG. 7.
FIG. 13 is a perspective view of the guard included in the first embodiment of a syringe safety device.
FIG. 14 is a top view of the guard of FIG. 13.
FIG. 15 is a bottom view of the guard of FIG. 13.
FIG. 16 is a side view of the guard of FIG. 13.
FIG. 17 is a first end view of the guard shown in FIG. 13 from the end that includes the slot.
FIG. 18 is a second end view of the guard shown in FIG. 13.
FIG. 19 is a perspective view of the lock included in the first embodiment of a syringe safety device.
FIG. 20 is a top view of the lock shown in FIG. 19.
FIG. 21 is a side view of the lock shown in FIG. 19.
FIG. 22 is an end view of the lock shown in FIG. 19.
FIG. 23 is a top view of the device of FIG. 1 in an undeployed configuration.
FIG. 24 is a bottom view of the device of FIG. 23.
FIG. 25 is a side view of the device of FIG. 23.
FIG. 26 is a first end view of the device shown in FIG. 23.
FIG. 27 is a second end view of the device shown in FIG. 23.
FIG. 28 is a perspective view of the device shown in FIG. 23.

DETAILED DESCRIPTION

The device described herein is a syringe safety device configured to be used with any standard syringe, such as a 3 ml syringe, and conventional needle, such as a needle under 2 inches long. The device is to be used as a deployable guard to reduce the chance of accidental needlestick injuries to healthcare workers while not incurring the cost of purchasing single use safety syringes. In embodiments, the device is made of stainless steel or another sterilizable material so that it may be autoclaved or otherwise sterilized for reuse.

Referring to the drawings, FIGS. 1-6 show a first embodiment of an assembled syringe safety device, which is generally designated as 10. The device 10 includes a shaft 12, a guard 13 and a lock 15. The figure shows the device in the "deployed" configuration, where the lock head 14 is caught and held by the bottom lock catch hole 20 (described below). This configuration is used after the injection has been given. The other configuration of the device is the "undeployed" configuration, shown in FIGS. 23-28, where the guard 13 and lock 15 are pushed into the shaft 12 along the spring housing 18 and the lock head 14 is caught and held in the top lock catch hole 22 (subcomponents mentioned described below). While FIG. 2 shows the length of the assembled syringe safety device in the deployed configuration as being about 130-131 mm, the device can be configured with other lengths.

FIGS. 7-12 show the details of the shaft 12. Subcomponents include the top lock catch hole, designated as 22; the bottom lock catch hole, designated as 20; the syringe finger flange holder, designated as 26; and the spring housing, designated by 18, 19. The top lock catch hole 22 is shaped to receive the lock head 14 from the interior of the shaft 12 and has a beveled edge on the exterior of the shaft 12 for easy pushing, meant to hold the lock component when the device is in the undeployed position. Bottom lock catch hole 20 is a hole that is shaped to fit the lock head 14 and is not beveled in order to reduce accidentally pushing in the lock head 14, meant to stop and hold the lock after deployment. Syringe finger flange holder 26 includes a thin space between two sets of two thin rectangular flanges 35, 36 that hold the finger flange of a syringe so that it is properly placed within the device, and will not fall out if inverted. The spring housing 18 includes a set of two tubular, elongated holes 28, 29 which are configured to receive the springs 40 that are used to deploy the guard 14, as well as the rails 30, 32 to the guard 13, which are described below. The spring 40 is shown in the spring housing 19. A similar spring (not shown) is used in the spring housing 18.

FIGS. 13-18 show the details of the guard 13. Subcomponents include the rails 30, 32, and a slot 34 which functions as a lock clearance space. In the embodiment shown, the rails 30, 32 include a set of two solid elongated cylinders configured to be inserted into the spring housing 18 described above, after the springs 40, 42 have been inserted. Between the rails 30, 32 and the spring housing 18, 19 is a certain amount of clearance which is subject to change depending on the tolerance of the fabrication method, and is meant to allow for unlubricated, unhindered sliding of the guard 13. Slot 34 is an elongated rectangular space created to allow the lock to bend past the guard 13 when the device is deployed and the lock is not present in either the bottom lock catch hole 20 or the top lock catch hole 22 in the shaft. 12. In the embodiment shown in FIGS. 7-12, the flanges have a length of about 28-29 mm and include a U-shaped opening with a width of about 11-12 mm, but other dimensions also can be used.

FIGS. 19-22 shown the details of the lock 15. Subcomponents include the lock head, designated by 14; and the guard mount, designated by 16. Lock head 14 is a rectangular protruding rectangular block on the front side of the lock 15 at a first end 36 of the lock 15 that is caught and held by the holes 2 and 4 of the shaft. Guard mount 16 is a smaller rectangular block mounted onto the guard to attach the two components. Guard mount 16 is positioned at a second end 38 of the lock 15 and protrudes slightly from the rear side of the lock. Guard mount 16 is meant to stop the guard 13 from leaving the shaft 12, and is retained after deployment.

The device 10 can be fabricated using appropriate machining or stereolithographic techniques for metal, such as stainless steel. Alternatively, the device can be formed from a thermoplastic or thermoset polymer, composite, or other suitable material. The device 10 is assembled by inserting two springs 40 into the spring housing 18, 19 of the shaft 12. In embodiments, the springs 40 are about 3 mm in diameter and between 10 and 50 mm in length, as long as the spring can compress sufficiently for the locking system to engage (i.e. for the lock head 14 to reach the upper hole 20 of the shaft 12). The lock 15 and guard 13 are to be attached, with the bottom of the lock 15 located 20 mm from the bottom of the guard. The guard 13 and lock 15 are then inserted into the shaft 12 with the top of the rails 30, 32 of the guard sliding into the spring shaft of the shaft. The device must first be pushed into the "Deployed" configuration, with the lock head 14 secured in the bottom lock catch hole 20 of the shaft. The lock head 14 must then be pushed into the device, unlocking the mechanism, and the guard 13 and lock 15 may then be pushed fully into the device 10 into the "Undeployed" configuration shown in FIGS. 23-28. There the lock head 14 is secured in the top lock catch hole 20 of the shaft 12 and the springs 40 are compressed. A non-safety, 3 ml syringe may now be inserted with the finger flanges placed in the syringe finger flange holder 26 of the shaft 12, and the barrel of the syringe on top of the inner part of the guard. The syringe may now be used in a normal manner. The device is then deployed by pushing the lock head 14 into the device 10 from this configuration, allowing the springs 40 to push the guard 12 and lock 15 downwards, and ending when the lock head 14 engages with the bottom lock catch hole 20 of the shaft. The syringe can now be ejected by gripping the top of the plunger and placing the syringe in a disposable sharps container. The device 10 may now be sterilized.

An embodiment of the device was tested using 3D stereolithographic printing comprising UV cured acrylic polymer and jet fusion nylon printing with nylon 12, though it is ultimately likely to be fabricated using stainless steel or another sterilizable material.

The device is a reusable, separate safety mechanism that is meant to be used in conjunction with a regular, non-safety syringe with the intent of lowering a facilities cost over time while protecting users from accidental needlestick injuries.

A number of alternatives, modifications, variations, or improvements therein may be subsequently made by those skilled in the art, which are also intended to be encompassed by the following claims.

What is claimed is:

1. A syringe safety device, comprising:
   a shaft configured to support a barrel of a syringe, the shaft having an elongated wall with a first aperture, and a second aperture longitudinally spaced from the first aperture,
   a guard configured to be disposed inside the shaft before the syringe is used and to extend outwardly from the shaft after the syringe is used, and
   a lock disposed between the guard and the shaft, the lock having a lock head disposed at a first end thereof, the lock head being disposed in the first aperture before the syringe is used and in the second aperture after the syringe is used.

2. The syringe safety device of claim 1, wherein the guard is configured to surround a needle after the syringe is used.

3. The syringe safety device of claim 1, wherein the guard has an elongated slot providing a clearance space for the lock.

4. The syringe safety device of claim 1, wherein the lock includes a guard mount disposed at a second end thereof, the guard mount being configured to keep the guard from leaving the shaft after use.

5. The syringe safety device of claim 1, wherein the shaft includes a flange holder configured to support a flange of the syringe during use of the device.

6. The syringe safety device of claim 5, wherein the flange holder comprises a first flange portion and a second flange portion.

7. The syringe safety device of claim 6, wherein the first flange portion and the second flange portion are configured to hold the flange of the syringe therebetween.

8. A method of giving an injection using the syringe safety device of claim 1.

9. The syringe safety device of claim 1, wherein the shaft comprises a spring housing including an elongated hole configured to receive a spring, the spring being used to deploy the guard.

10. A syringe safety device, comprising:
    a shaft configured to support a barrel of a syringe, the shaft having an elongated wall with a first aperture, and a second aperture longitudinally spaced from the first aperture,
    a flange holder configured to hold a flange of the syringe, the flange holder comprising a first flange pair and a second flange pair each including a first flange portion and a second flange portion separated by a space,
    a guard configured to be disposed inside the shaft before the syringe is used and to extend outwardly from the shaft after the syringe is used, and
    a lock disposed between the guard and the shaft, the lock having a lock head disposed at a first end thereof, the lock head being disposed in the first aperture before the syringe is used and in the second aperture after the syringe is used.

11. The syringe safety device of claim 10, wherein the lock includes a guard mount disposed at a second end thereof, the guard mount being configured to keep the guard from leaving the shaft after use.

12. The syringe safety device of claim 10, wherein the shaft comprises a spring housing including an elongated hole configured to receive a spring, the spring being used to deploy the guard.

13. A method of giving an injection using the syringe safety device of claim 10.

\* \* \* \* \*